(12) United States Patent
Okawa et al.

(10) Patent No.: US 9,470,614 B2
(45) Date of Patent: Oct. 18, 2016

(54) METHOD FOR IMPACT-TESTING CHEMICALLY STRENGTHENED GLASS, METHOD FOR REPRODUCING CRACKS IN CHEMICALLY STRENGTHENED GLASS, AND METHOD FOR MANUFACTURING CHEMICALLY STRENGTHENED GLASS

(71) Applicant: ASAHI GLASS COMPANY, LIMITED, Chiyoda-ku (JP)

(72) Inventors: Hiroyuki Okawa, Tokyo (JP); Kazuhiko Yamanaka, Tokyo (JP)

(73) Assignee: ASAHI GLASS COMPANY, LIMITED, Chiyoda-ku (JP)

( * ) Notice: Subject to any disclaimer, the term of this patent is extended or adjusted under 35 U.S.C. 154(b) by 131 days.

(21) Appl. No.: 14/172,061

(22) Filed: Feb. 4, 2014

(65) Prior Publication Data

US 2014/0150525 A1 Jun. 5, 2014

Related U.S. Application Data

(63) Continuation of application No. PCT/JP2012/069369, filed on Jul. 30, 2012.

(30) Foreign Application Priority Data

Aug. 4, 2011 (JP) ................... 2011-171197

(51) Int. Cl.
  *G01N 3/00* (2006.01)
  *G01N 19/02* (2006.01)
  *G01N 3/303* (2006.01)
  *G01M 7/08* (2006.01)

(52) U.S. Cl.
  CPC ............ *G01N 3/303* (2013.01); *G01M 7/08* (2013.01)

(58) Field of Classification Search
  CPC .. G01N 3/30; G01N 3/303; G01N 2203/001; G01N 2203/006; G01N 2203/0062; G01N 2203/0064; G01N 2203/0066; G01M 7/08; G01M 3/48; G01M 5/0033
  USPC .................... 73/12.06, 12.11, 12.13
  See application file for complete search history.

(56) References Cited

U.S. PATENT DOCUMENTS 4,074,992 A * 2/1978 Voss ............... C03C 21/002
                                                         501/57
5,773,148 A * 6/1998 Charrue .............. C03C 3/085
                                                         428/410

(Continued)

FOREIGN PATENT DOCUMENTS

JP     61044554 U * 3/1986 .............. G01N 3/30
JP     03-146843     6/1991

(Continued)

OTHER PUBLICATIONS

Author: unknown, Title: D4551-12, Standard Specification for Poly(Vinyl Chloride) (PVC) Plastic Flexible Concealed Water-Containment Membrane, Date: Nov. 2012, Last previous edition approved in 2008 as D4551-96(2008, Publisher: ASTM Committee D20 on Plastics, pp. 11.*

*Primary Examiner* — Lisa Caputo
*Assistant Examiner* — Roger Hernandez-Prewit
(74) *Attorney, Agent, or Firm* — Oblon, McClelland, Maier & Neustadt, L.L.P.

(57) ABSTRACT

A chemically strengthened glass is disposed on a base, and an impacting object is dropped from above in a state where one surface of the chemically strengthened glass is in contact with an abrasive surface of a sandpaper containing an abrasive having a size of not smaller than a depth of a compressive stress layer.

12 Claims, 18 Drawing Sheets

(56) References Cited

U.S. PATENT DOCUMENTS

| | | |
|---|---|---|
| 6,766,046 B1 | 7/2004 | Saito et al. |
| 2006/0142412 A1* | 6/2006 | Yamaoka ............. B32B 7/12 523/111 |
| 2008/0318028 A1* | 12/2008 | Winstanley ....... B32B 17/10036 428/332 |
| 2010/0028607 A1* | 2/2010 | Lee ..................... C03C 3/093 428/156 |
| 2010/0167059 A1 | 7/2010 | Hashimoto et al. |

FOREIGN PATENT DOCUMENTS

| | | |
|---|---|---|
| JP | 11-132929 | 5/1999 |
| JP | 11-316179 | 11/1999 |
| JP | 2003-249181 A | 9/2003 |
| JP | 2009-7243 A | 1/2009 |
| JP | 2010-243387 | 10/2010 |
| JP | 2011-105598 | 6/2011 |
| JP | 2011-136895 A | 7/2011 |

* cited by examiner

FIG. 17

Sandpaper P30

| | 4g | 9g | 17g | 29g |
|---|---|---|---|---|
| 90cm | | Spider Cracking | Spider Cracking | Spider Cracking |
| 60cm | Slow Cracking | Spider Cracking | | |
| 30cm | Slow Cracking | Slow Cracking | OK / NG Slow Cracking | Slow Cracking |

FIG. 18

| Sandpaper P100 | 4g | 9g | 17g | 29g |
|---|---|---|---|---|
| 90cm | | Slow Cracking | | Spider Cracking |
| 60cm | No fracture | No fracture | Slow Cracking | Slow Cracking |
| 30cm | No fracture | No fracture | No fracture | No fracture |

METHOD FOR IMPACT-TESTING CHEMICALLY STRENGTHENED GLASS, METHOD FOR REPRODUCING CRACKS IN CHEMICALLY STRENGTHENED GLASS, AND METHOD FOR MANUFACTURING CHEMICALLY STRENGTHENED GLASS

TECHNICAL FIELD

The present invention relates to a method for impact-testing a chemically strengthened glass having a compressive stress layer formed by chemical strengthening, a method for reproducing cracks in a chemically strengthened glass, and a method for manufacturing a chemically strengthened glass.

BACKGROUND ART

Recently, in order to increase the protection and aesthetic appearance of a display in a flat panel display device such as mobile phone and personal digital assistance (PDA), a thin plate-shaped cover glass having a region wider than an image display portion is provided on the front surface of a display. Reduction in the weight and thickness is required for such a flat panel display device, and to meet this requirement, the cover glass used for protecting a display is also required to achieve reduction in its thickness. However, if the thickness of the cover glass is reduced, the strength decreases, and there arises a problem that the cover glass itself may be cracked by the falling or the like during use or carrying and the primary role of protecting a display device may not be fulfilled.

For this reason, in the conventional cover glass, the flaw resistance of the cover glass has been increased by chemically strengthening a glass plate to thereby form a compressive stress layer on the surface (for example, Patent Document 1).

However, if the cover glass encounters an impact as in the case where the user drops a flat panel display device by mistake, a slow crack that is a crack growing in the glass at a relatively slow rate from a flaw penetrating a compressive stress layer is sometimes initiated even in a chemically strengthened cover glass (hereinafter, such a cracking manner of glass is referred to as "slow cracking").

RELATED ART

Patent Document

Patent Document 1: JP-A-2011-105598

SUMMARY OF THE INVENTION

Problems that the Invention is to Solve

In studying the above-described slow cracking and developing a cover glass resistant to slow cracking, it has been heretofore very difficult to reproduce slow cracking. Specifically, it was necessary that after fabricating a flat panel display device, a considerable number of devices fabricated are dropped on the ground or the like and thereby fractured, and the glass accidentally developing slow cracking are extracted by evaluating the cracked glasses.

However, dropping a flat panel display device which is an actual product on the ground to reproduce slow cracking is not only inefficient but also wastes the flat panel display device itself. For this reason, it has been demanded to reproduce slow cracking in a chemically strengthened glass before the flat panel display device becomes a product.

Therefore, an object of the present invention is to provide a method for impact-testing a chemically strengthened glass, which can reproduce slow cracking in a chemically strengthened glass, a method for reproducing a crack in a chemically strengthened glass, and a method for manufacturing a chemically strengthened glass.

Means for Solving the Problems

In the course of investigation and study of the slow cracking, the present inventors have elucidated the mechanism of slow cracking and accomplished the present invention.

The present invention provides the following aspects.

(1) A method for impact-testing a chemically strengthened glass having formed on a surface thereof a compressive stress layer, the method comprising disposing the chemically strengthened glass on a base, and dropping an impacting object from above in a state where one surface of the chemically strengthened glass is in contact with an abrasive surface of a sandpaper containing an abrasive having a size of not smaller than a depth of the compressive stress layer.

(2) The method for impact-testing a chemically strengthened glass according to (1), wherein the sandpaper is disposed on the upper side of the chemically strengthened glass.

(3) The method for impact-testing a chemically strengthened glass according to (1) or (2), wherein an anti-scattering film is placed on another surface of the chemically strengthened glass, the another surface being not in contact with the abrasive surface of the sandpaper.

(4) A method for reproducing a crack in a chemically strengthened glass having formed on a surface thereof a compressive stress layer, the method comprising giving an impact on the chemically strengthened glass to thereby make a flaw having a depth larger than the compressive stress layer.

(5) The method for reproducing a crack in a chemically strengthened glass according to (4), wherein the chemically strengthened glass is disposed on a base and an impacting object is dropped from above in a state where one surface of the chemically strengthened glass is in contact with an abrasive surface of a sandpaper containing an abrasive having a size of not smaller than a depth of the compressive stress layer.

(6) The method for reproducing a crack in a chemically strengthened glass according to (5), wherein the sandpaper is disposed on the upper side of the chemically strengthened glass.

(7) The method for reproducing a crack in a chemically strengthened glass according to (5) or (6), wherein an anti-scattering film is placed on another surface of the chemically strengthened glass, the another surface being not in contact with the abrasive surface of the sandpaper.

(8) The method for reproducing a crack in a chemically strengthened glass according to (4), wherein an impacting object which has a tapered tip with a length not smaller than a depth of the compressive stress layer and has a hardness higher than that of the chemical strengthened glass is made to collide with one surface of the chemically strengthened glass.

(9) The method for reproducing a crack in a chemically strengthened glass according to (8), wherein an anti-scattering film is placed on another surface of the chemically strengthened glass, with which the impacting object is not made to collide.

(10) A method for manufacturing a chemically strengthened glass having formed on a surface thereof a compressive stress layer, the method comprising:

determining a threshold value by the method for impact-testing a chemically strengthened glass sheet as described in any one of (1) to (3) by changing a drop height of a sphere, and performing a sampling inspection of judging a quality of the chemically strengthened glass based on the threshold value.

Advantages of the Invention

According to the method for impact-testing a chemically strengthened glass described in (1) above, slow cracking initiated in a flat panel display device can be reproduced and in turn, slow cracking can be initiated by using only a chemically strengthened glass without actually dropping a flat panel display device itself, so that this method can be utilized for development or the like of a new glass material. In addition, thanks to using sandpaper that is easily available at a low cost, the cost of the impact test can be reduced.

Also, according to the method for impact-testing a chemically strengthened glass described in (2) above, a state close to the state of a flat panel display device which has been dropped on the ground can be created, and reproducibility of slow cracking can be enhanced.

Furthermore, according to the method for impact-testing a chemically strengthened glass described in (3) above, observation of a chemically strengthened glass cracked is facilitated.

According to the method for reproducing a crack in a chemically strengthened glass described in (4) above, slow cracking initiated in a flat panel display device can be reproduced and in turn, slow cracking can be initiated by using only a chemically strengthened glass without actually dropping a flat panel display device itself, so that this method can be utilized for development or the like of a new glass material.

Also, according to the method for reproducing a crack in a chemically strengthened glass described in (5) above, thanks to using sandpaper that is easily available at a low cost, the cost for reproducing slow cracking can be reduced.

Furthermore, according to the method for reproducing a crack in a chemically strengthened glass described in (6) above, a state close to the state of a flat panel display device which has been dropped on the ground can be created, and reproducibility of slow cracking can be enhanced.

In addition, according to the method for reproducing a crack in a chemically strengthened glass described in (7) above, observation of a chemically strengthened glass cracked is facilitated.

Moreover, according to the method for reproducing a crack in a chemically strengthened glass described in (8) above, the impacting object can be repeatedly used, so that the cost for reproducing slow cracking can be reduced.

Also, according to the method for reproducing a crack in a chemically strengthened glass described in (9) above, observation of a chemically strengthened glass cracked is facilitated.

According to the method for manufacturing a chemically strengthened glass described in (10) above, the slow cracking resistance performance on dropping of a flat panel display device can be controlled.

BRIEF DESCRIPTION OF THE DRAWINGS

FIG. 17 is a photograph of a chemically strengthened glass cracked in the method for reproducing slow cracking, in which sandpaper of P30 ($D_3$: 710 μm) is used.

FIG. 18 is a photograph of a chemically strengthened glass cracked in the method for reproducing slow cracking, in which sandpaper of P100 ($D_3$: 180 μm) is used.

MODE FOR CARRYING OUT THE INVENTION

The method for reproducing a crack of a chemically strengthened glass of the present invention is described below, but first of all, the mechanism of slow cracking initiated when of a flat panel display device falls, which has been found by the present inventors, is described below.

Figure 1:
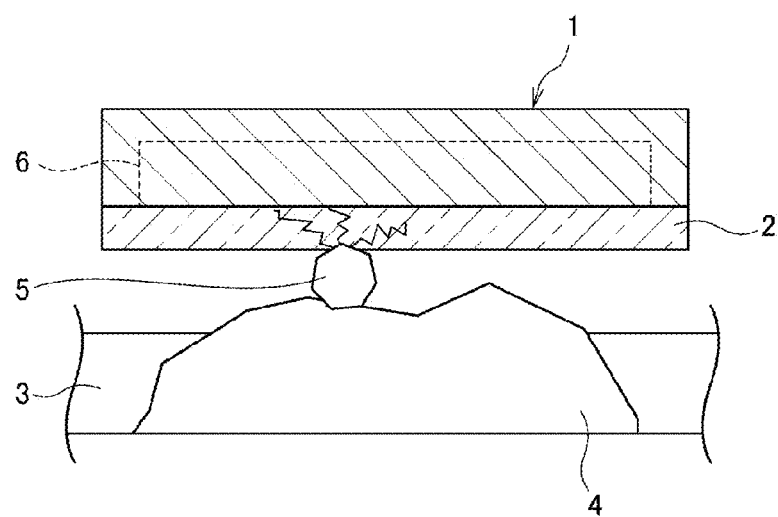
FIG. 1 is a schematic view illustrating a situation where slow cracking is initiated in the cover glass when of a flat panel display device falls.
Figure 2A:
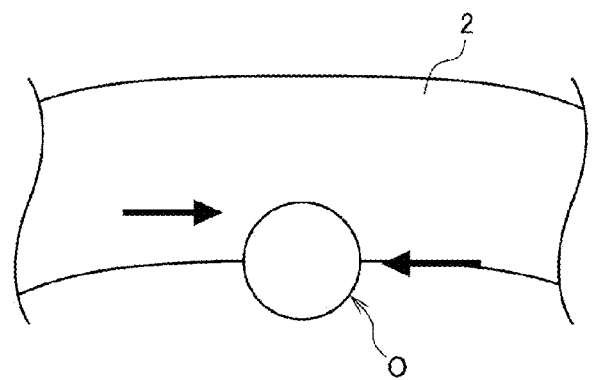
FIG. 2($a$) is a schematic view showing a fracture origin on initiation of slow cracking, and FIG. 2($b$) is a schematic view showing a crack initiated from the fracture origin in FIG. 2($a$).
Figure 2B:
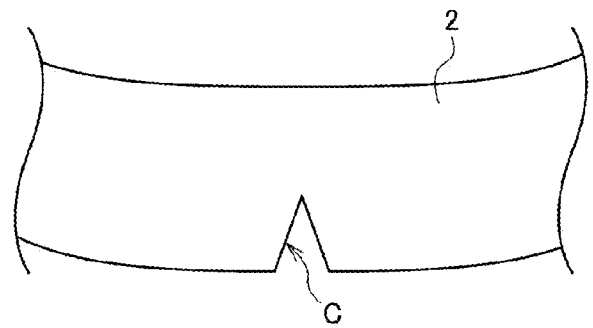
Figure 3A:
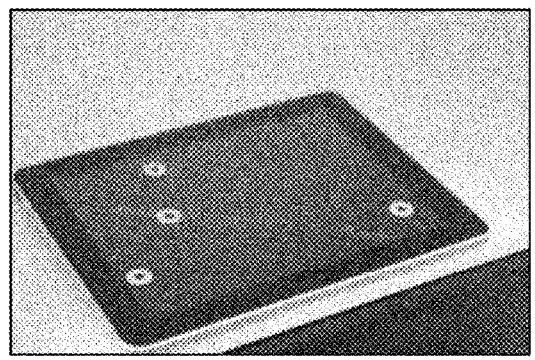
FIG. 3($a$) is a view showing a photograph of a flat panel display device where slow cracking is initiated, FIG. 3($b$) is a view showing a magnified photograph of a fracture origin viewed from above, and FIG. 3($c$) is a view showing a photograph of a fracture origin viewed from the side.
Figure 3B:
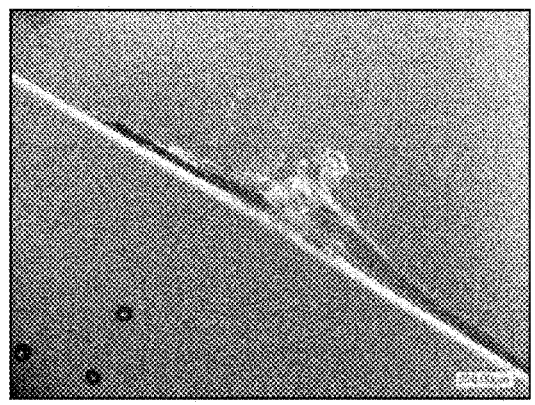

FIG. 1 is a schematic view illustrating a situation where slow cracking is initiated in the cover glass when of a flat panel display device falls; FIG. 2(a) is a schematic view showing a fracture origin on initiation of slow cracking; FIG. 2(b) is a schematic view showing a crack initiated from the fracture origin in FIG. 2(a); FIG. 3(a) is a view showing a photograph of a flat panel display device where slow cracking is initiated; FIG. 3(b) is a view showing a magnified photograph of a fracture origin viewed from above; and FIG. 3(c) is a view showing a photograph of a fracture origin viewed from the side.

In a flat panel display device 1, a substantially rectangular frame is provided to surround an image display part 6, and a cover glass is supported on the frame. As shown in FIG. 1, when a flat panel display device falls on the ground (asphalt/concrete) and is brought into contact with a sand 5 or the like on a small stone 4 in the asphalt/concrete 3 in the state where the cover glass 2 faces down, a compressive stress acts on a fracture origin O, and a tensile stress acts on the periphery thereof (FIG. 2(a)). Subsequently, a tensile stress acts on the fracture origin O, and a crack C extends, as a result, the cover glass 2 is cracked (FIG. 2(b)). A fracture origin may occur in the central part of the cover glass, but in many cases, the fracture origin occurs in a part of a region supported by the frame, because deflection of the cover glass is constrained by the frame.

Figure 3C:
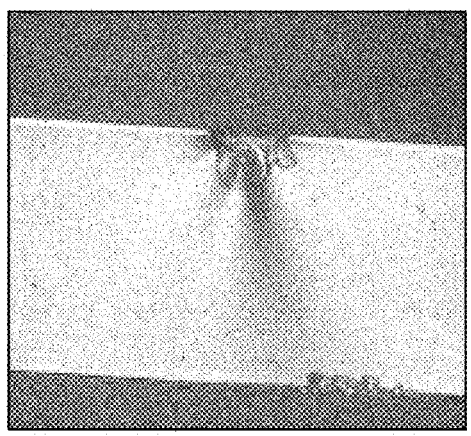

As apparent from the fracture surface in FIG. 3(c), the fracture origin of the crack above of the cover glass is a flaw having a depth larger than the compressive stress layer. In FIGS. 3(a) and 3(b), one crack extends from the fracture origin to split the cover glass into two parts. When the fracture surface shown in FIG. 3(c) is further examined, a mirror that is smooth like a mirror and has a long mirror radius is observed around the fracture origin occurred at a position deeper than the depth of the compressive stress layer.

Figure 4:
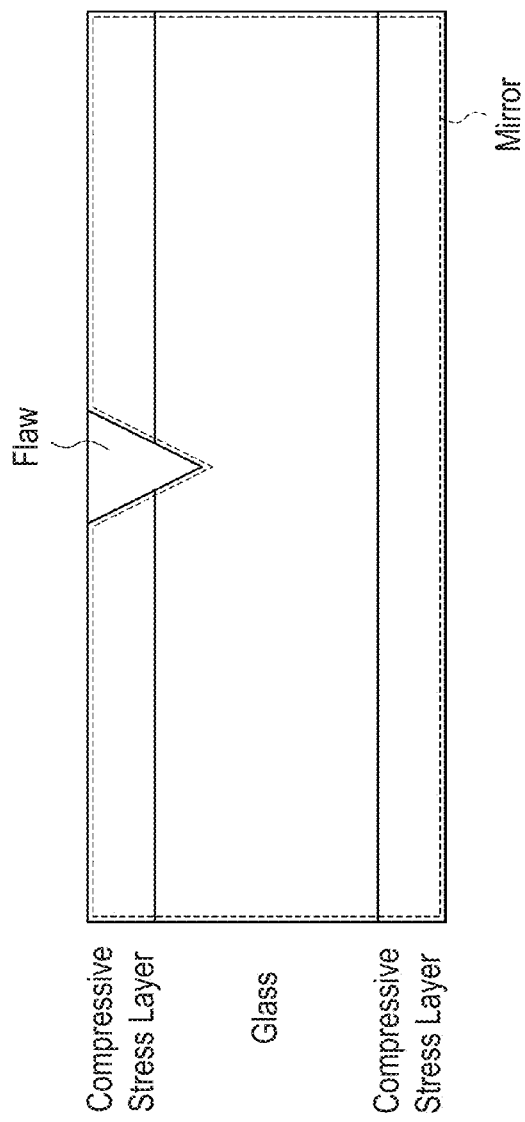
FIG. 4 is a view schematically showing the fracture surface in FIG. 3($c$).

FIG. 4 is a view schematically showing the fracture surface in FIG. 3(c). The fracture surface reflects the process of fracture, that is, factors such as fracture origin, developing direction of fracture, and whether the fracture is developed slowly or rapidly. According to the analysis of this fracture surface of slow cracking, the mirror having a long mirror radius suggests that the fracture is developed by a small stress, and such a smooth fracture surface suggests that a crack is slowly grown at a speed by far slower than the sound velocity. Therefore, according to the fracture surface in FIG. 3(c), it is understood that after an origin is formed at a position deeper than the depth of the compressive stress layer in the cover glass, a crack is slowly grown and the fracture is developed by a small stress. In the cover glass cracked by such slow cracking, the number of cracked pieces is from several pieces to (depending on the case) several tens of pieces. The number of cracked pieces is typically from 2 to 20, and the example in which one crack is extended from the fracture origin shown in FIGS. 3(a) and 3(b) and the cover glass is split into two parts, is a symbolic example of slow cracking.

More microscopically, whether the crack is caused by slow cracking or not is judged as follows. First, a crack of which fracture origin is not identified cannot be said to be the case of slow cracking. Also, when a flaw penetrating the compressive stress layer, that is, a flaw having a depth larger than the compressive stress layer (so-called DOL), is confirmed to be the fracture origin by observing the vicinity of the fracture origin, the crack is caused by slow cracking.

Furthermore, when the mirror radius is long and the fracture surface is the mirror with no mist or hackle, the crack is caused by slow cracking.

As described above, it is very difficult to reproduce slow cracking, and even if a cover glass is dropped on the ground, slow cracking may accidentally occur, but reproducibility is not obtained. That is, the crack that is not caused by slow cracking (hereinafter, sometimes referred to as "non-slow cracking") occurs in many cases, and cover glasses are wasted.

Figure 5:
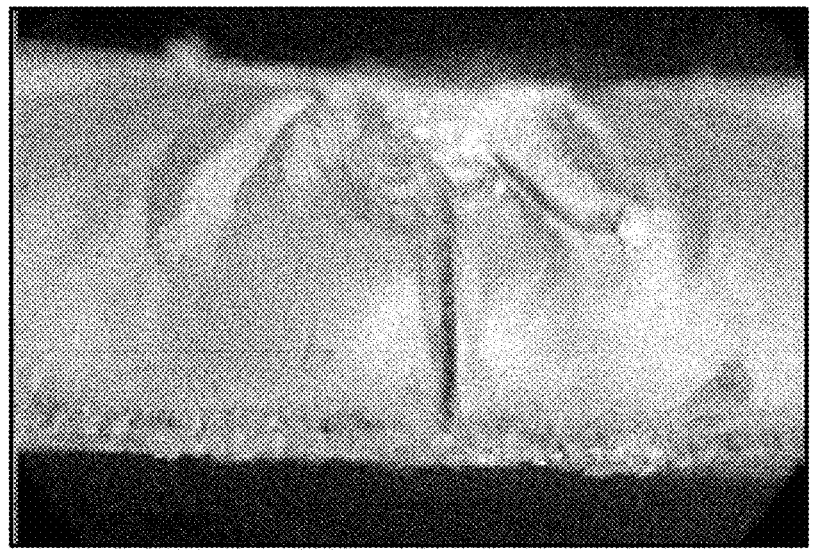
FIG. 5 is a view showing a side-view photograph of a fracture origin of a cover glass where non-slow cracking is initiated.
Figure 6:
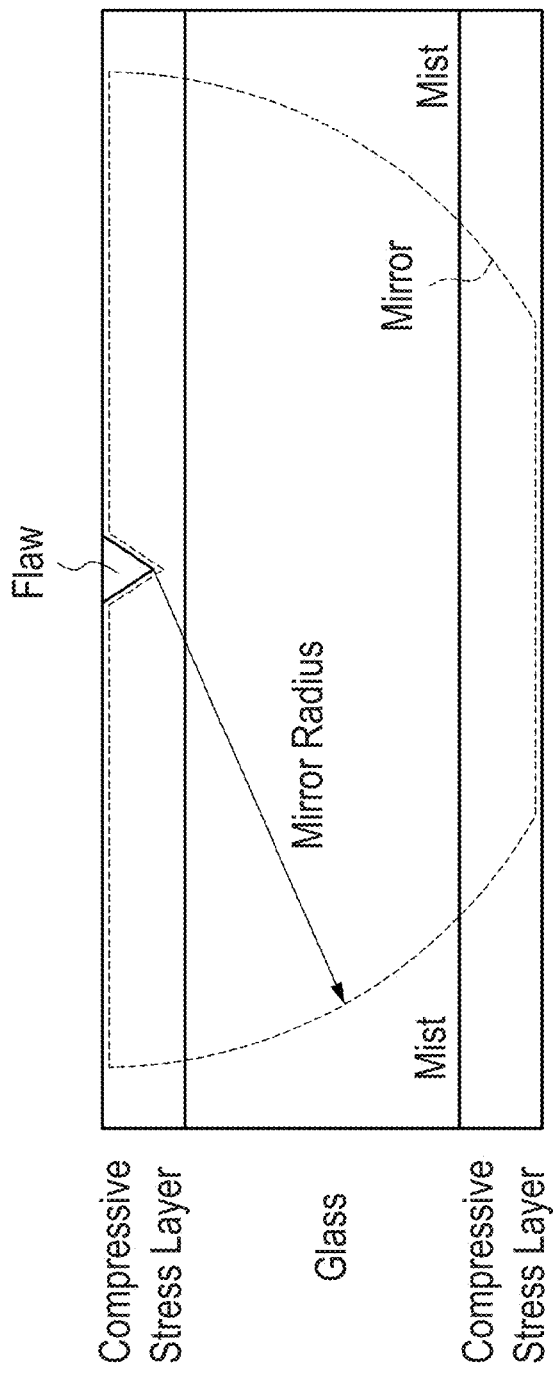
FIG. 6 is a view schematically showing the fracture surface in FIG. 5.

As the non-slow cracking in contrast to slow cracking, the crack of a cover glass caused by pushing a Knoop indenter into the glass surface is described. FIG. 5 is a view showing a side-view photograph of a fracture origin of a cover glass by non-slow cracking, and FIG. 6 is a view schematically showing the fracture surface in FIG. 5.

Observing the fracture surface of this non-slow cracking, a fracture origin is formed in the compressive stress layer, a mirror that is smooth like a mirror and has a short mirror radius is observed around the fracture origin, and a mist is present around the mirror. According to the analysis of this fracture surface of non-slow cracking, the mirror having a short mirror radius suggests that a fracture is developed by a large stress, and the mist suggests that the crack is rapidly grown. Therefore, according to the fracture surface in FIG. 5, it is understood that after a fracture origin is formed at a position shallower than the depth of the compressive stress layer in the cover glass, the fracture is developed by a large stress and a crack is rapidly grown. Once non-slow cracking is initiated, as shown in FIG. 15(e), the cover glass is broken into a plurality of glass pieces (20 pieces or more) due to a plurality of cracks extending in a spider web pattern (hereinafter, such a cracking manner is referred to as "spider cracking"). In this way, it is understood that fracture is initiated in quite a different mode between the slow cracking and the non-slow cracking.

With respect to the non-slow cracking, since a fracture origin occurs in the compressive stress layer, it is effective for preventing this crack by increasing the surface compressive stress or increasing the thickness of the compressive stress layer. However, in the slow cracking, a fracture origin occurs in the region beyond the compressive stress layer (the depth of a flaw is typically from several tens to several hundreds of micrometers and the thickness of the compressive stress layer by chemical strengthening is from several to several tens of micrometers) and therefore, a cover glass having mechanical characteristics resistant to slow cracking must be developed. In this meaning, reproduction of slow cracking in a chemically strengthened glass used as a cover glass is very important to proceed with future research and development.

Therefore, the present inventors have found a method for reproducing the slow cracking above. The slow cracking means that, as described above, the crack initiation results from formation of a fracture origin at a position deeper than the depth of the compressive stress layer. Typically, the number of cracked pieces is from 2 to 20. In other words, non-slow cracking initiated from an origin in the compressive stress layer results in shattered glass pieces and therefore, is caused by an utterly different mode.

First Embodiment

Figure 7:
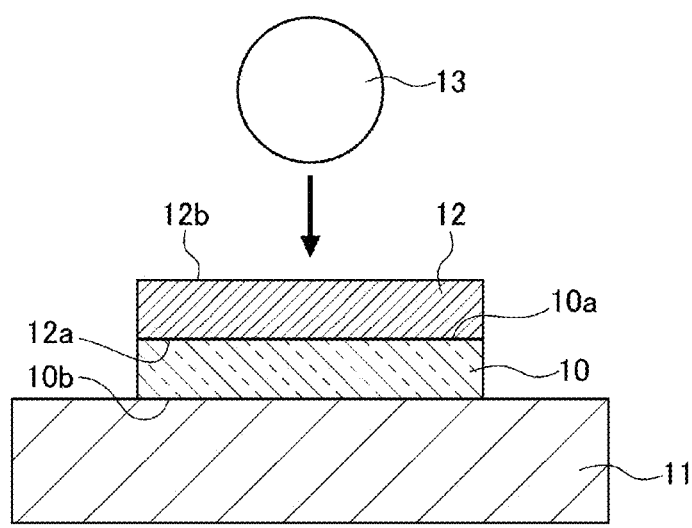
FIG. 7 is a schematic view of the method for reproducing slow cracking in the first embodiment.

In the method for reproducing slow cracking in the first embodiment, as shown in FIG. 7, a chemically strengthened glass 10 having formed on the surface thereof a compressive stress layer is disposed on a base 11, the chemically strengthened glass 10 is brought into contact with the abrasive surface 12a of sandpaper 12 containing an abrasive having a size of not smaller than the depth of the compressive stress layer, and a sphere 13 such as iron sphere is dropped from above. At this time, the sandpaper 12 is preferably disposed on the upper side of the chemically strengthened glass 10, the top surface 10a of the chemically strengthened glass 10 is in contact with the abrasive surface 12a of the sandpaper 12, and the sphere 13 falls on the surface 12b opposite the abrasive surface 12a of the sandpaper 12.

The base 11 is preferably formed of a hard stone such as granite. Thanks to such a stone, a stress relief space can be eliminated, similarly to the region of a cover glass supported by a frame, in which a flaw working out to a fracture origin is likely to occur. However, the material of the base 11 can be changed by adjusting the elastic modulus or deflection according to the purpose, and a straight material, glass, a center-bored flame or the like may be appropriately selected.

The sandpaper for use in the present invention is not limited to polishing paper (abrasive paper, JIS R6252:2006) but encompasses those obtained by coating an abrasive on a backing through an adhesive, and comparable articles, for example, abrasive cloth (JIS R6251:2006) and waterproof abrasive paper (JIS R6253:2006).

As the sandpaper 12, articles having ratings of P12 to P2500 according to the grit size of the abrasive contained are present (JIS R6252, 2006). The abrasive is typically alumina or silicon carbide. Assuming that the grit diameter of sand contained in the asphalt/concrete is from 0.06 to 1 mm, this substantially corresponds to P30 to P600 as the grit size of the abrasive contained in the sandpaper 12.

According to JIS R6010, 2006, in the grit size distribution of an abrasive of P30 that is a fine power, the oversize quantity $Q_1$ of 1st stage (first-stage sieve opening=1.18 mm) is 0%, the cumulative oversize quantity $Q_2$ of 1st+2nd stages (second-stage sieve opening=850 μm) is 1% or less, the cumulative oversize quantity $Q_3$ of 1st+2nd+3rd stages (third-stage sieve opening=710 μm) is 14±4%, the cumulative oversize quantity $Q_4$ of 1st+2nd+3rd+4th stages (fourth-stage sieve opening=600 μm) is 61±9%, the cumulative oversize quantity $Q_5$ of 1st+2nd+3rd+4th+5th stages (fifth-stage sieve opening=500 μm) is 92% or more, and the undersize quantity $\Delta Q$ of fifth-stage sieve is 8% or less; and in the grit size distribution of an abrasive of P600 that is a coarse grit, the maximum grit diameter $d_s$-0 is 72 μm or less, the grit diameter $d_s$-3 at a cumulative sedimentation height of 3% is 43.0 μm or less, the grit diameter $d_s$-50 at a cumulative sedimentation height of 50% is 25.8±1.0 μm, and the grit diameter $d_s$-95 at a cumulative sedimentation height of 95% is 18.0 μm or more.

With respect to the size of the abrasive used in the present invention, in the case where the sandpaper is in accordance with JIS R6252, 2006, the abrasive size is the third-stage sieve opening $D_3$ specified in Table 2 of JIS R6010, 2006 for the coarse grit of P12 to P220 and the upper-limit grid diameter $d_3$ at a cumulative sedimentation height of 3% specified in Table 3 of JIS R6010, 2006 for the fine powder of P240 to P2500, and in the case where the sandpaper is not in accordance with JIS R6252, 2006, the abrasive size is the maximum grit diameter.

For example, assuming that the depth of the compressive stress layer is 30 μm, sandpaper of, for example, P30 ($D_3$: 710 μm), P100 ($D_3$: 180 μm), P320 ($d_3$: 66.8 μm) or P600 ($d_3$: 43.0 μm) is selected as the sandpaper containing an abrasive larger than the depth of the compressive stress layer.

The sandpaper in which the size of the abrasive is larger than the depth of the compressive stress layer is typically sandpaper in which the fourth-stage sieve opening $D_4$ of the abrasive, the grit diameter $d_s$-50 at a cumulative sedimentation height of 50%, or the average grit diameter is larger than the depth of the compressive stress layer.

The material and weight of the sphere 13 can be varied according to the purpose but typically, an SUS-made stainless steel sphere of 4 to 150 g is used.

In this way, the sphere 13 is dropped on the chemically strengthened glass 10 disposed on the base 11, whereby a fracture origin O occurs in the chemically strengthened glass 10 at a position deeper than the depth of the compressive stress layer on the top surface 10a side due to an abrasive contained in the sandpaper 12.

Figure 8A:
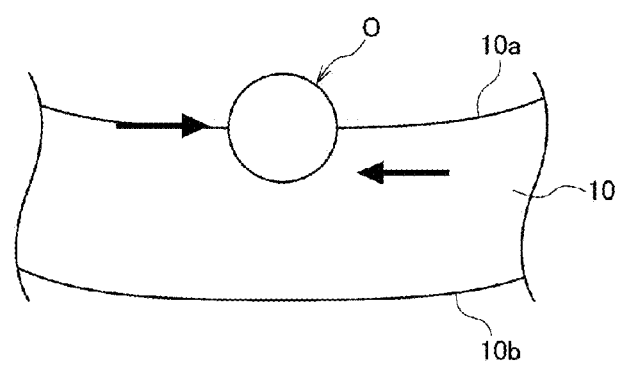
FIG. 8($a$) is a schematic view showing a fracture origin when cracking is initiated in a chemically strengthened glass in the method for reproducing slow cracking in FIG. 7, and FIG. 8($b$) is a schematic view showing a crack initiated from the fracture origin in FIG. 8($a$).
Figure 8B:
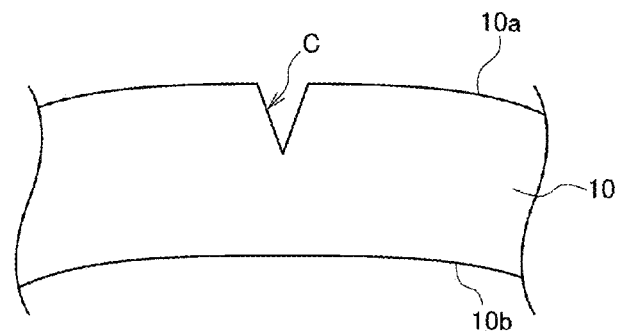

At this time, a compressive stress acts on the fracture origin O, and a tensile stress acts on the periphery thereof (FIG. 8(a)). Subsequently, a tensile stress acts on the fracture origin O, and a crack C extends, as a result, the cover glass is cracked (FIG. 8(b)). That is, despite the difference in the surface of fracture origin between top surface and bottom surface, the crack is initiated by the same mechanism as the slow cracking described in FIGS. 2(a) and 2(b).

Figure 13A:
FIGS. 13($a$) to 13($c$) are views showing a photograph of a chemically strengthened glass cracked in Examples 1 to 3.
Figure 14:
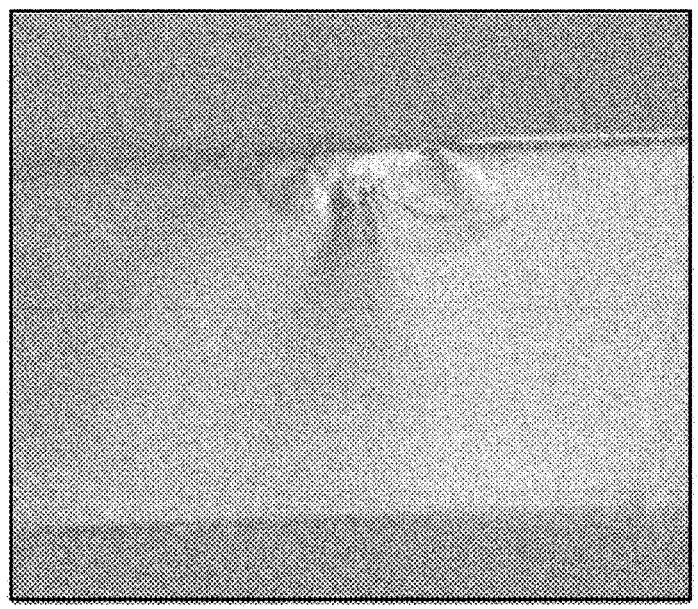
FIG. 14 is a view showing a photograph of a fracture origin in Example 1 viewed from the side.

FIG. 13(a) is a view showing a photograph of a cover glass in which slow cracking is initiated by dropping an iron sphere 13 of 28 g and ϕ0.75 inches from a height of 50 mm after disposing sandpaper 12 of P30 on the upper side of a chemically strengthened glass 10, and FIG. 14 is a view showing a photograph of the fracture origin viewed from the side.

The chemically strengthened glass is split into 3 parts, but FIG. 14 shows the same fracture surface as in FIG. 3(c), and it is understood that the crack is initiated by the same mechanism as the slow cracking.

In this way, the chemically strengthened glass is observed with an eye at every dropping of the sphere and, for example, whether a crack is initiated in the chemically strengthened glass or the glass is not cracked is observed. In the case of performing the impact test of samples by changing the sphere drop height, a Weibull plot is created by repeating the measurement typically from 10 to 20 times, and the chemically strengthened glass can be evaluated by the maximum, minimum or average fracture height, the gradient of Weibull plot, and the like. If desired, the cracking manner of the entire chemically strengthened glass or the surface/cross-section of the fracture origin is observed/photographed by using an optical microscope, a laser microscope or the like, and the cracking modes are classified.

Figure 9:
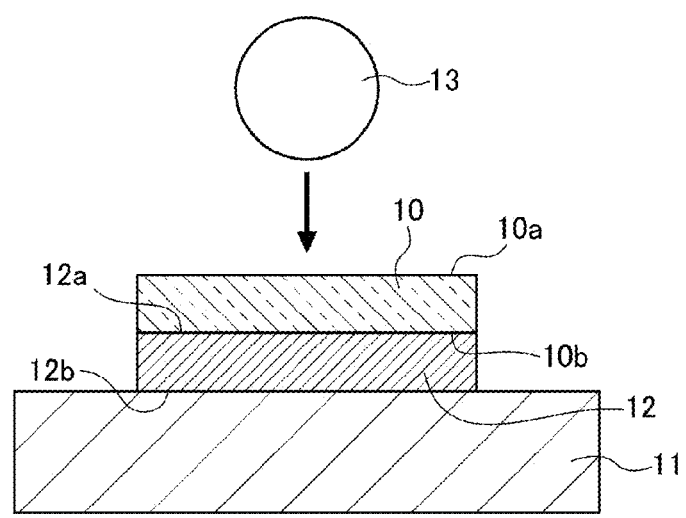
FIG. 9 is a schematic view of the method for reproducing slow cracking in a modified example.

FIG. 9 shows a modified example of the first embodiment.

In this modification, as shown in FIG. 9, sandpaper 12 containing an abrasive having a size of not smaller than the depth of the compressive stress layer is disposed on the lower side of a chemically strengthened glass 10, the bottom surface 10b of the chemically strengthened glass 10 is in contact with the abrasive surface 12a of the sandpaper 12, and a sphere 13 is dropped on the top surface 10a of the chemically strengthened glass 10.

By dropping the sphere 13 on the thus-arranged chemically strengthened glass 10, a fracture origin O occurs in the chemically strengthened glass 10 at a position deeper than the depth of the compressive stress layer on the bottom surface 10b side due to an abrasive contained in the sandpaper 12.

Figure 10A:
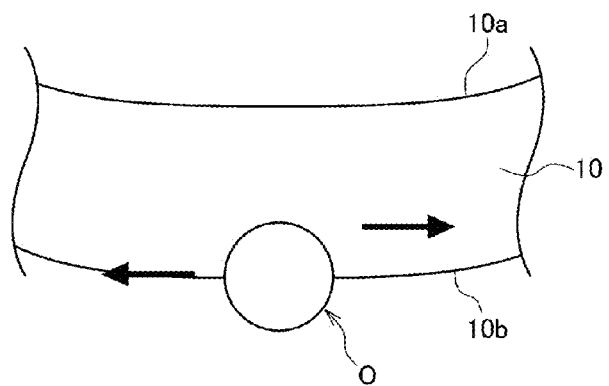
FIG. 10($a$) is a schematic view showing a fracture origin when cracking is initiated in a chemically strengthened glass in the method for reproducing slow cracking in FIG. 9, and FIG. 10($b$) is a schematic view showing a crack initiated from the fracture origin in FIG. 10($a$).
Figure 10B:
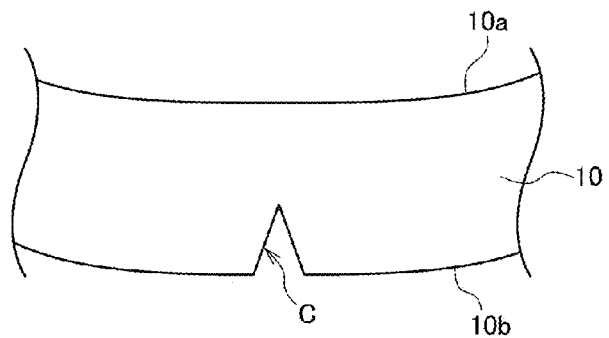

At this time, a tensile stress acts on fracture origin O (FIG. 10(a)), and a crack C extends from the origin, as a result, the chemically strengthened glass 10 is cracked (FIG. 10(b)).

Accordingly, this method is the same as the first embodiment in that an origin occurs at a position deeper than the depth of the compressive stress layer and a crack is initiated, but differs in that a tensile stress acts on the fracture origin O when the sphere 13 is dropped.

Figure 15A:
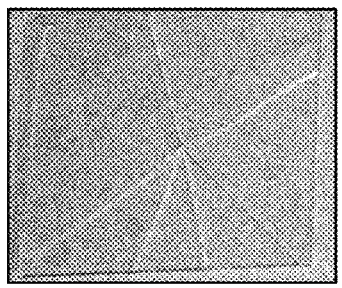
FIGS. 15($a$) to 15($e$) are views showing a photograph of a chemically strengthened glass cracked in Examples 4 to 7 and Comparative Example 1.
Figure 15B:
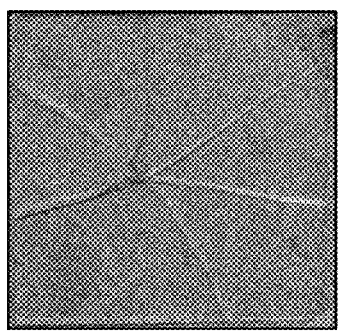
Figure 15C:
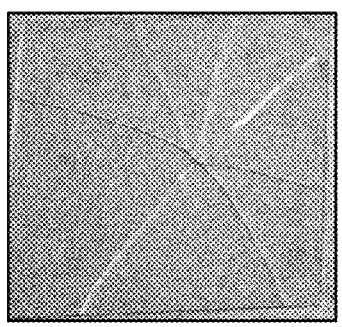
Figure 15D:
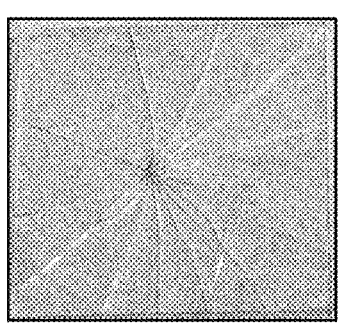
Figure 15E:
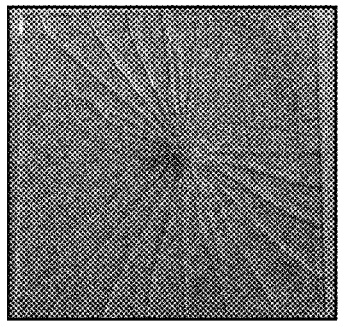
Figure 16:
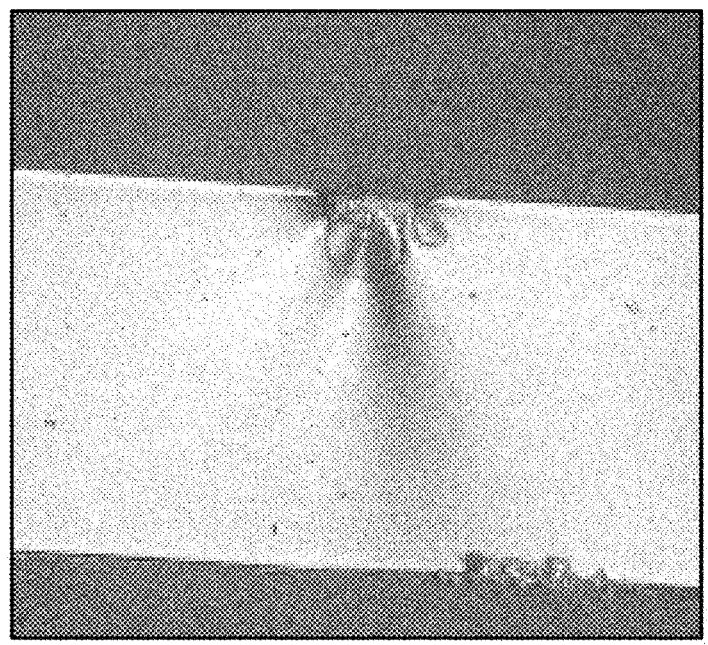
FIG. 16 is a photograph of a fracture origin in Example 4 viewed from the side.

FIG. 15(b) is a view showing a photograph of a cover glass in which slow cracking is initiated by dropping a sphere 13 of 28 g and ϕ0.75 inches from a height of 25 mm after disposing sandpaper 12 of P30 on the lower side of a chemically strengthened glass 10, and FIG. 16 is a view showing a photograph of the fracture origin viewed from the side.

The chemically strengthened glass is split into 6 parts, but FIG. 16 shows the same fracture surface as in FIG. 3(c), and it is understood that the crack is initiated by the same mechanism as the slow cracking.

Second Embodiment

Figure 11:
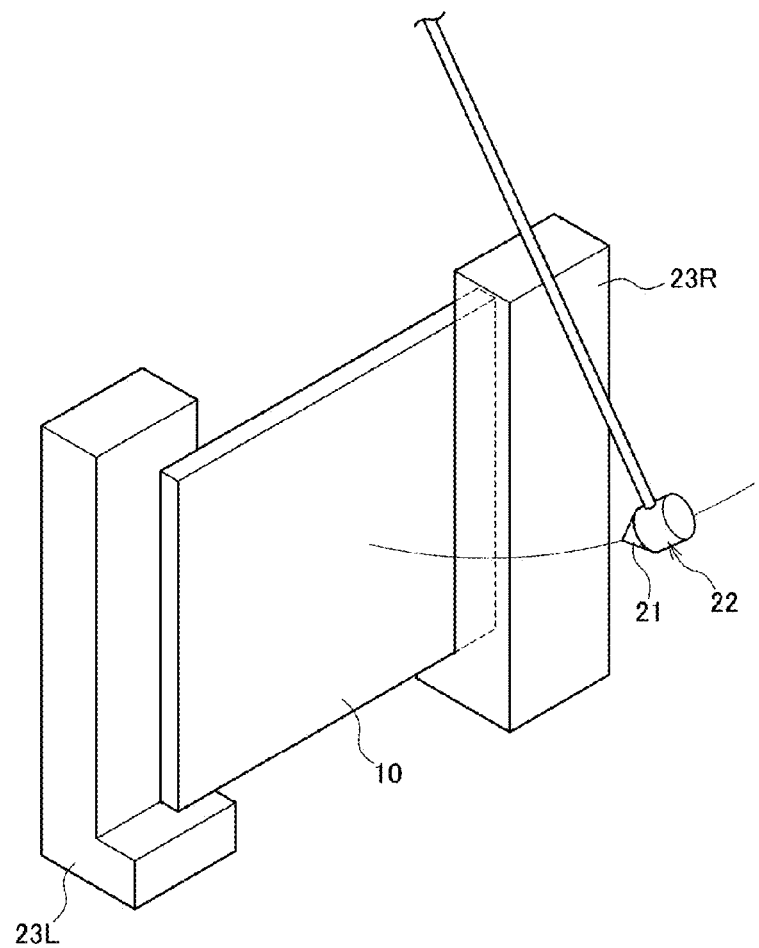
FIG. 11 is a schematic view of the method for reproducing slow cracking in the second embodiment.

In the method for reproducing slow cracking in the second embodiment, as shown in FIG. 11, with respect to a chemically strengthened glass 10 having formed on the surface thereof a compressive stress layer, an impacting object 22 having a tapered tip part 21 not shorter than the depth of the compressive stress layer and having a hardness higher than that of the chemically strengthened glass 10 is made to collide with the chemically strengthened glass 10.

In this embodiment, the chemically strengthened glass 10 is vertically supported by supporting members 23L and 23R having a substantially L-shaped cross-section and being disposed on the right and left, and the impacting object 22 composed of an ultrahard material and having a missile-shaped tip part 21 is moved like a pendulum. By causing the impacting object 22 to collide with the thus-arranged chemically strengthened glass 10, a fracture origin occurs in the chemically strengthened glass 10 at a position deeper than the depth of the compressive stress layer of the collision surface.

At this time, a compressive stress acts on the fracture origin, a tensile stress acts on the periphery thereof, a tensile stress then acts on the fracture origin, and a crack extends, as a result, the cover glass is cracked. Thus, the crack is initiated by the same mechanism as the slow cracking described in FIGS. 2(a) and 2(b). In this embodiment, as long as a fracture origin can be caused to occur in a chemically strengthened glass at a position deeper than the depth of the compressive stress layer by causing an impacting object having a tapered tip part not shorter than the depth of the compressive stress layer and having a hardness higher than that of the chemically strengthened glass to collide with the chemically strengthened glass, any configuration can be employed.

Also, in these first and second embodiments, observation of the fracture surface of the chemically strengthened glass cracked is facilitated by placing an anti-scattering film for preventing scattering of the cracked glass, on the surface (in FIG. 7, the bottom surface 10b of the chemically strengthened glass 10; in FIG. 9, the top surface 10a of the chemically strengthened glass 10; and in FIG. 11, the surface opposite the surface with which the impacting object 22 collides) opposite the surface where a fracture origin O is formed. In the case where prevention of shattering is not required, the anti-scattering film need not necessarily be placed.

Chemical strengthening of the chemically strengthened glass of the present invention is performed, for example, by dipping the glass in a potassium nitrate ($KNO_3$) molten salt at 435° C. for 4 hours. The depth of the compressive stress layer is preferably 15 μm or more, more preferably 30 μm or more. Also, the compressive stress of the chemically strengthened glass is preferably 600 MPa or more, more preferably 700 MPa or more.

The chemically strengthened glass has a thickness of 1.5 mm or less, preferably from 0.3 to 1.1 mm. Also, for example, glass having the following composition is used.

(i) A glass containing, as the composition expressed in terms of mol %, from 50 to 80% of $SiO_2$, from 2 to 25% of $Al_2O_3$, from 0 to 10% of $Li_2O$, from 0 to 18% of $Na_2O$, from 0 to 10% of $K_2O$, from 0 to 15% of MgO, from 0 to 5% of CaO and from 0 to 5% of $ZrO_2$. Here, for example, the term "containing from 0 to 10% of $K_2O$" means that $K_2O$ is not essential but may be contained in the range up to 10% as long as the object of the present invention is not impaired (hereinafter, the same).

(ii) A glass containing, as the composition expressed in terms of mol %, from 50 to 74% of $SiO_2$, from 1 to 10% of $Al_2O_3$, from 6 to 14% of $Na_2O$, from 3 to 11% of $K_2O$, from 2 to 15% of MgO, from 0 to 6% of CaO and from 0 to 5% of $ZrO_2$, in which the total content of $SiO_2$ and $Al_2O_3$ is 75% or less, the total content of $Na_2O$ and $K_2O$ is from 12 to 25%, and the total content of MgO and CaO is from 7 to 15%.

(iii) A glass containing, as the composition expressed in terms of mol %, from 68 to 80% of $SiO_2$, from 4 to 10% of $Al_2O_3$, from 5 to 15% of $Na_2O$, from 0 to 1% of $K_2O$, from 4 to 15% of MgO and from 0 to 1% of $ZrO_2$.

(iv) A glass containing, as the composition expressed in terms of mol %, from 67 to 75% of $SiO_2$, from 0 to 4% of $Al_2O_3$, from 7 to 15% of $Na_2O$, from 1 to 9% of $K_2O$, from 6 to 14% of MgO and from 0 to 1.5% of $ZrO_2$, in which the total content of $SiO_2$ and $Al_2O_3$ is from 71 to 75%, the total content of $Na_2O$ and $K_2O$ is from 12 to 20%, and in the case of containing CaO, the content thereof is less than 1%.

EXAMPLES

Examples of the present invention are described below.

Glass for chemical strengthening having a thickness of 0.7 mm and a size of 50 mm×50 mm was produced by a float process and chemically strengthened by dipping the glass in a potassium nitrate ($KNO_3$) molten salt at 435° C. for 4 hours. The surface compressive stress after chemical strengthening was about 800 MPa, and the depth of the compressive stress layer was about 45 μm. The chemically strengthened glass after chemical strengthening was transported in a cassette so as to prevent scratching of the surface or keep the surface from coming into contact with others and an anti-scattering film was placed on the surface opposite the surface working out to a fracture origin.

Figure 12A:
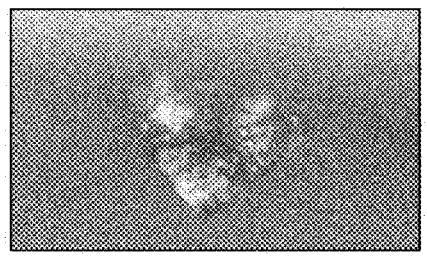
FIG. 12($a$) is a view showing a magnified photograph of sandpaper of P30, FIG. 12($b$) is a view showing a magnified photograph of asphalt/concrete, and FIG. 12($c$) is a graph showing a tip angle distribution of sandpaper of P30 and a tip angle distribution of sand.
Figure 12B:
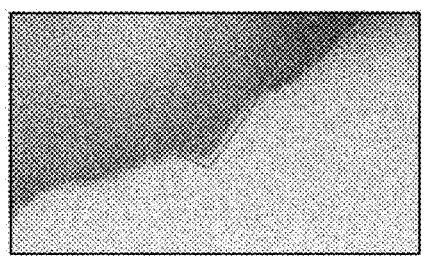
Figure 12C:
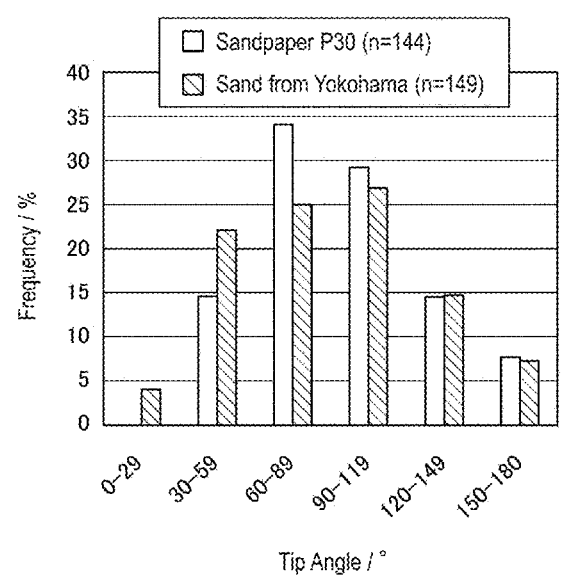

This chemically strengthened glass was subjected to cracking by the method of the first embodiment. More specifically, sandpaper (abrasive cloth called sheet paper) was disposed on the upper side of the chemically strengthened glass such that the top surface of the chemically strengthened glass came into contact with the abrasive surface of the sandpaper, and an SUS-made sphere of ϕ0.75 inches and 28 g was dropped on the surface opposite the abrasive surface of the sandpaper. Also, sandpaper of P30 ($D_3$: 710 μm) was used as the sandpaper, and in Examples 1 to 3, the sphere drop height was changed, that is, the sphere drop height was set to 50 mm in Example 1, the sphere drop height was set to 100 mm in Example 2, and the sphere drop height was set to 150 mm in Example 3, and then, the fracture surface and cracking manner of the chemically strengthened glass were observed. FIG. 12(a) is a magnified photograph of the sandpaper of P30; FIG. 12(b) is a magnified photograph of asphalt/concrete (sampled in Yokohama); and FIG. 12(c) is a graph showing a tip angle distribution of sandpaper of P30 and a tip angle distribution of sand. In FIG. 12(c), after observing each sandpaper at 144 portions and observing the sand at 149 portions, the tip angle of sandpaper or sand is indicated on the abscissa, and the frequency is indicated on the ordinate. Because of approximation of the shape between alumina as the abrasive contained in the sandpaper of P30 and the small stone or the like contained in the asphalt/concrete, sandpaper of P30 was selected in Examples 1 to 3, out of sandpapers containing an abrasive having a size not smaller than the depth of the compressive stress layer.

FIGS. 13 and 14 show the results.

Figure 13B:
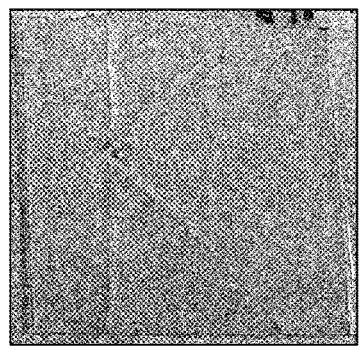
Figure 13C:
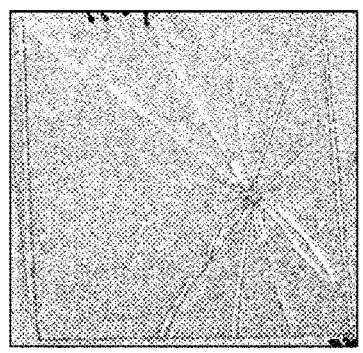

As seen from FIGS. 13(a) to 13(c), in all of Examples 1 to 3, the number of glass pieces was 20 or less. Also, examining the fracture surface shown in FIG. 14, a flaw at a position deeper than the depth of the compressive stress layer occurred as a fracture origin, and a mirror being smooth like a mirror and having a long mirror radius was observed around the fracture origin, whereby slow cracking could be reproduced in Examples 1 to 3. Also, comparison of Examples 1 to 3 leads to the result that as the sphere drop height is lower, the number of cracked glass pieces decreases.

Subsequently, the same chemically strengthened glass as the chemically strengthened glass above was subjected to cracking by a modified method of the first embodiment. More specifically, sandpaper was disposed on the lower side of the chemically strengthened glass such that the bottom surface of the chemically strengthened glass came into contact with the abrasive surface of the sandpaper, and an SUS-made sphere of ϕ0.75 inches and 28 g was dropped on the top surface of the chemically strengthened glass. The mesh of the sandpaper and the sphere drop height were changed as shown in Table 1, and then, the fracture surface and cracking manner of the chemically strengthened glass were observed.

TABLE 1

| | Mesh | Iron Sphere Drop Height |
|---|---|---|
| Example 4 (FIG. 15 (a)) | P30 ($D_3$: 710 μm) | 25 mm |
| Example 5 (FIG. 15 (b)) | P30 ($D_3$: 710 μm) | 50 mm |
| Example 6 (FIG. 15 (c)) | P100 ($D_3$: 180 μm) | 25 mm |
| Example 7 (FIG. 15 (d)) | P100 ($D_3$: 180 μm) | 50 mm |
| Comparative Example 1 (FIG. 15 (e)) | P600 ($d_3$: 43.0 μm) | 50 mm |

FIGS. 15 and 16 show the results.

As seen from FIGS. 15(a) to 15(d), in all of Examples 4 to 7, the number of glass pieces was 20 or less. Also, examining the fracture surface shown in FIG. 16, a fracture origin was formed at a position deeper than the depth of the compressive stress layer, a smooth fracture surface was present around the fracture origin, and a mirror being smooth like a mirror and having a long mirror radius was observed further therearound, whereby slow cracking could be reproduced in Examples 4 to 7. Also, comparison of Example 4 with Example 5 or comparison of Example 6 with Example 7 leads to the result that as the sphere drop height is lower, the number of cracked glass pieces decreases. Furthermore, comparison of Example 4 with Example 6 or comparison of Example 5 with Example 7 leads to the result that as the mesh is smaller, namely, as the grit diameter is larger, the number of cracked glass pieces decreases.

On the other hand, in Comparative Example 1, as shown in FIG. 15(e), the number of glass pieces is 20 or more, and a facture surface could not be observed. It is considered that this is because in the case of sandpaper of P600, the size of the abrasive contained in the sandpaper is 43 μm or less in terms of the grit diameter and the length of the abrasive protruding from the surface of the sandpaper is smaller than that, as a result, a fracture origin was formed in the compressive stress layer. Accordingly, the crack in Comparative Example 1 is regarded as non-slow cracking (spider cracking).

Furthermore, the same chemically strengthened glass as the chemically strengthened glass above was subjected to cracking by a modified method of the first embodiment, where an SUS-made sphere was dropped on the top surface of the chemically strengthened glass while changing the mesh of the sandpaper, the sphere drop height, and the weight of the sphere. Three stages of height of 30 cm, 60 cm and 90 cm were used as the sphere drop height, and spheres having four kinds of weight of 4 g, 9 g, 17 g and 29 g were used as the sphere.

FIG. 17 is a photograph of a chemically strengthened glass cracked in the method for reproducing slow cracking, in which sandpaper of P30 ($D_3$: 710 μm) was used, and FIG. 18 is a photograph of a chemically strengthened glass cracked in the method for reproducing slow cracking, in which sandpaper of P100 ($D_3$: 180 μm) was used.

In the Figures, "slow cracking" means that the crack is identified as being caused by slow cracking by the analysis of fracture surface, "spider cracking" means that the crack is identified as being caused by non-slow cracking (spider cracking) by the analysis of fracture surface, and if not particularly specified, this indicates that the crack could not be identified whether it is caused by slow cracking or non-slow cracking. Also, "no fracture" indicates that the crack was not initiated in the glass.

It is understood from FIGS. 17 and 18 that as the drop height becomes higher, non-slow cracking (spider cracking) is more likely to be initiated than slow cracking, and as the weight of sphere is increased, non-slow cracking (spider cracking) is more likely to be initiated than slow cracking. Also, in the case of using sandpaper of P100 ($D_3$: 180 μm), if the drop height was low and/or the weight of sphere was light, the crack was not initiated.

As demonstrated by these results, according to the above-described method for reproducing slow cracking, slow cracking could be initiated by using only a chemically strengthened glass without actually dropping a flat panel display device itself. This method can be utilized for development or the like of a new glass material resistant to slow cracking. In addition, thanks to using sandpaper that is easily available at a low cost, the inspection cost can be reduced.

Furthermore, as the method for producing a chemically strengthened glass, when the above-described method is incorporated in the production line and when a sphere is dropped on a chemically strengthened glass while changing the sphere drop height, and then, a threshold value is determined, and a sampling inspection of judging the quality of the chemically strengthened glass is performed based on the threshold value, the slow cracking resistance performance of a cover glass can be controlled.

The present invention is not limited to the above-described embodiments and can be implemented in various modes without departing from the gist of the invention.

This application is based on Japanese Patent Application No. 2011-171197 filed on Aug. 4, 2011, the contents of which are incorporated herein by way of reference.

DESCRIPTION OF REFERENCE NUMERALS AND SIGNS

2 Cover glass
3 Asphalt/concrete
4 Small stone
5 Sand
10 Chemically strengthened glass
10a Top surface
11 Base
12 Sandpaper
12a Abrasive surface
13 Sphere
O Fracture origin
C Crack

The invention claimed is:

1. A method for impact-testing a flat chemically strengthened glass having formed on a surface thereof a compressive stress layer,
the method comprising disposing the chemically strengthened glass on a base, and dropping a sphere from above in a state where one surface of the chemically strengthened glass is in contact with an abrasive surface of a sandpaper containing an abrasive having a size of not smaller than a depth of the compressive stress layer, wherein said sphere makes contact with a surface of said sandpaper which is opposite said abrasive surface.

2. The method for impact-testing a flat chemically strengthened glass according to claim 1, wherein the sandpaper is disposed such that the abrasive surface is in contact with a surface of the chemically strengthened glass which is opposite the surface of the chemically strengthened glass that is in contact with said base.

3. The method for impact-testing a flat chemically strengthened glass according to claim 2, wherein an anti-scattering film is placed on another surface of the chemically strengthened glass, the another surface being not in contact with the abrasive surface of the sandpaper.

4. The method for impact-testing a flat chemically strengthened glass according to claim 1, wherein an anti-scattering film is placed on another surface of the chemically strengthened glass, the another surface being not in contact with the abrasive surface of the sandpaper.

5. A method for reproducing a crack in a flat chemically strengthened glass having formed on a surface thereof a compressive stress layer,
the method comprising giving an impact on the chemically strengthened glass to thereby make a flaw having a depth larger than the compressive stress layer,
wherein the chemically strengthened glass is disposed on a base and a sphere is dropped from above in a state where one surface of the chemically strengthened glass is in contact with an abrasive surface of a sandpaper containing an abrasive having a size of not smaller than a depth of the compressive stress layer,
wherein said sphere makes contact with a surface of said sandpaper which is opposite said abrasive surface.

6. The method for reproducing a crack in a flat chemically strengthened glass according to claim 5, wherein the sandpaper is disposed such that the abrasive surface is in contact with a surface of the chemically strengthened glass which is opposite the surface of the chemically strengthened glass that is in contact with said base.

7. The method for reproducing a crack in a flat chemically strengthened glass according to claim 6, wherein an anti-scattering film is placed on another surface of the chemically strengthened glass, the another surface being not in contact with the abrasive surface of the sandpaper.

8. The method for reproducing a crack in a flat chemically strengthened glass according to claim 5, wherein an anti-scattering film is placed on another surface of the chemically strengthened glass, the another surface being not in contact with the abrasive surface of the sandpaper.

9. A method for manufacturing a chemically strengthened glass having formed on a surface thereof a compressive stress layer, the method comprising:
determining a threshold value by the method for impact-testing a flat chemically strengthened glass sheet by changing a drop height of a sphere
wherein said method for impact-testing a flat chemically strengthened glass sheet comprises disposing the chemically strengthened glass on a base, and dropping said sphere from a predetermined height above the chemically strengthened glass, wherein surface of the chemically strengthened glass is in contact with an abrasive surface of a sandpaper containing an abrasive having a size of not smaller than a depth of the compressive stress layer, wherein said sphere makes contact with a surface of said sandpaper which is opposite said abrasive surface, and
performing a sampling inspection of judging a quality of the chemically strengthened glass based on the threshold value.

10. The method according to claim 9, wherein the sandpaper is disposed such that the abrasive surface is in contact with a surface of the chemically strengthened glass which is opposite the surface of the chemically strengthened glass that is in contact with said base.

11. The method according to claim 10, wherein an anti-scattering film is placed on another surface of the chemically strengthened glass, the another surface being not in contact with the abrasive surface of the sandpaper.

12. The method according to claim 9, wherein an anti-scattering film is placed on another surface of the chemically strengthened glass, the another surface being not in contact with the abrasive surface of the sandpaper.

* * * * *